United States Patent [19]

Durden et al.

[11] 4,111,955

[45] Sep. 5, 1978

[54] N-TRIHALOMETHANESULFENYL CARBAMOYLOXIMINO DI-SULFUR HETEROCYCLIC COMPOUNDS

[75] Inventors: John Apling Durden; Themistocles Damasceno Joaquim D'Silva, both of, S. Charleston, W. Va.

[73] Assignee: Union Carbide Corporation, New York, N.Y.

[21] Appl. No.: 688,222

[22] Filed: May 20, 1976

Related U.S. Application Data

[62] Division of Ser. No. 364,138, May 25, 1923, Pat. No. 3,992,549.

[51] Int. Cl.$^2$ .................. C07D 339/00; C07D 339/06; C07D 339/08

[52] U.S. Cl. .................. 260/327 M; 260/327 R; 260/327 P

[58] Field of Search ............ 260/327 P, 327 M, 327 R

[56] References Cited

U.S. PATENT DOCUMENTS

| | | | |
|---|---|---|---|
| 3,193,561 | 7/1965 | Addor | 260/327 |
| 3,467,672 | 9/1969 | Addor | 260/327 |
| 3,819,649 | 6/1974 | Zumach et al. | 260/327 M |
| 3,956,500 | 5/1976 | Durden et al. | 424/276 |

*Primary Examiner*—Richard L. Raymond
*Attorney, Agent, or Firm*—Robert C. Brown

[57] ABSTRACT

Certain N-polyhaloalkanesulfenyl carbamoyloximino di-sulfur containing heterocyclic compounds have exceptional pesticidal properties and low mammalian toxicity.

14 Claims, No Drawings

N-TRIHALOMETHANESULFENYL CARBAMOYLOXIMINO DI-SULFUR HETEROCYCLIC COMPOUNDS

This application is a division of our copending U.S. patent application Ser. No. 364,138, filed May 25, 1973 now U.S. Pat. No. 3,992,549.

This invention relates to methods and compositions for combating insects. In another aspect, this invention relates to certain N-polyhaloalkanesulfenyl substituted carbamoyloximino heterocyclic compositions which are novel per se.

The compounds which are employed as the active ingredients in the pesticidal compositions of this invention are the heterocyclic compounds corresponding to the following general formula:

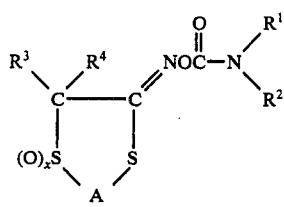

wherein: $R^1$ is lower alkyl having from 1 to 4 carbon atoms, phenyl or phenyl substituted with one or more halogen, acylamido, methylthio, methoxy, or alkyl substituents having from 1 to 4 carbon atoms or a methylenedioxy group; $R^2$ is trihalomethanesulfenyl; $R^3$ and $R^4$ are the same or different and are hydrogen, lower alkyl having from 1 to 6 carbon atoms, lower alkenyl having from 2 to 6 carbon atoms, halogen substituted alkyl having from 1 to 6 carbon atoms, alkoxyalkyl having a total of from 2 to 6 carbon atoms, alkylthioalkyl, alkylsulfinylalkyl or alkylsulfonylalkyl, having a total of from 2 to 6 carbon atoms, phenyl or phenyl substituted with one or more halogen, methoxy or lower alkyl substituents having from 1 to 4 carbon atoms; A is methylene, ethylene, propylene, ethenylene, propenylene or methylene, ethylene, propylene, ethenylene or propenylene substituted with one or more alkyl groups having from 1 to 3 carbon atoms; and $x$ is 0, 1 or 2.

The compositions of this invention can be prepared conveniently in accordance with the following general reaction scheme:

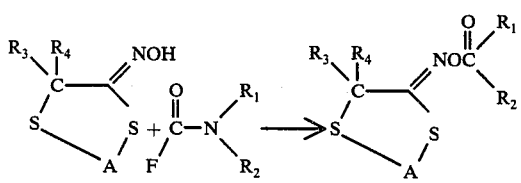

where A, $R_1$, $R_2$, $R_3$ and $R_4$ are as defined above.

The oxime precursors used in the synthesis described above, can be prepared in the manner described in copending U.S. patent application Ser. No. 254,271, filed May 17, 1972. The appropriate N-trihalomethane sulfenylcarbamoyl fluoride composition used in this synthesis can be prepared conveniently by the method described in U.S. Pat. No. 3,639,471.

The following compositions are illustrative of the new compositions of this invention:

4-[(N-methyl-N-trichloromethanesulfenyl) carbamoyloximino]-1,3-dithiolane
2,2-dimethyl-4-[(N-methyl-N-trichloromethanesulfenyl)-carbamoyloximino]-1,3-dithiolane
2-Methyl-4-[(N-methyl-N-trichloromethanesulfenyl)-carbamoyloximino]-1,3-dithiolane
5-Methyl-4-[(N-methyl-N-trichloromethanesulfenyl) carbamoyloximino]-1,3-dithiolane
5,5-Dimethyl-4-[(N-methyl-N-trichloromethanesulfenyl)-carbamoyloximino]-1,3-dithiolane
2-[(N-methyl-N-trichloromethanesulfenyl) carbamoyloximino]-1,4-dithiane
3,3-Dimethyl-2-[(N-methyl-N-trichloromethanesulfenyl)-carbamoyloximino]-1,4-dithiane
3-Propyl-2-[(N-methyl-N-trichloromethanesulfenyl)-carbamoyloximino]-1,4-dithiane
3-Isopropyl-2-[(N-methyl-N-trichloromethanesulfenyl)-carbamoyloximino]-1,4-dithiane
3-Allyl-2-[(N-methyl-N-trichloromethanesulfenyl)-carbamoyloximino]-1,4-dithiane
3-(2-Methoxyethyl)-2-[(N-methyl-N-trichloromethanesulfenyl)-carbamoyloximino]-1,4-dithiane
2-[(N-ethyl-N-trichloromethanesulfenyl) carbamoyloximino]-1,4-dithiane
2-[(N-methyl-N-trifluoromethanesulfenyl) carbamoyloximino]-1,4-dithiane
3,3,5-Trimethyl-2-[(N-methyl-N-trichloromethanesulfenyl)-carbamoyloximino]-1,4-dithiane
3,3-Dimethyl-2-[(N-methyl-N-trichloromethanesulfenyl)-carbamoyloximino]-1,4-dithi-5-ene
2-[(N-methyl-N-trichloromethanesulfenyl) carbamoyloximino]-1,4-dithi-5-ene
3,3-Dimethyl-2-[(N-methyl-N-trichloromethanesulfenyl)-carbamoyloximino]-1,4-dithiacycloheptane
4-[N-(4-acetamidophenyl)-N-(trifluoromethanesulfenyl) carbamoyloximino]-5-methyl-1,3-dithiolane
2-[N-(4-methylthiophenyl)-N-(trichloromethanesulfenyl) carbamoyloximino]-1,4-dithiane
2-[N-methyl-N-chlorodifluoromethanesulfenyl) carbamoyloximino]-1,4-dithiane
2-[(N-methyl-N-trichloromethanesulfenyl) carbamoyloximino]-1,4-dithiacyclohept-6-ene
4-[(N-methyl-N-trifluoromethanesulfenyl) carbamoyloximino]-1,3-dithiolane
2-[(N-phenyl-N-trichloromethanesulfenyl) carbamoyloximino]-1,4-dithiane
2-[(N-butyl-N-trichloromethanesulfenyl) carbamoyloximino]-1,4-dithiane
2-[(N-methyl-N-fluorodichloromethanesulfenyl) carbamoyloximino]-1,4-dithiane
3-(3,4-Methylenedioxyphenyl)-2-[(N-methyl-N-trichloromethanesulfenyl)-carbamoyloximino]-1,4-dithiane
3-(4-Chlorophenyl)-2-[(N-methyl-N-trichloromethanesulfenyl)-carbamoyloximino]-1,4-dithiane
3-(2-Chloroethyl)-2-[(N-methyl-N-trichloromethanesulfenyl)-carbamoyloximino]-1,4-dithiane
2-[(N-methyl-N-trichloromethanesulfenyl)-carbamoyloximino]-1,4-dithiane-4-oxide
2-[(N-methyl-N-trichloromethanesulfenyl)-carbamoyloximino]-1,4-dithiane-4,4-dioxide The following examples are illustrative of the procedures used for preparing the compounds of this invention.

EXAMPLE I

PREPARATION OF 2-[(N-METHYL-N-TRICHLOROMETHANESULFENYL)-CARBAMOYLOXIMINO]-1,4-DITHIANE

To a solution of 1.35 g of 2-oximino-1,4-dithiane and 2.05 g of N-methyl-N-trichloromethanesulfenyl-carbamylfluoride in 75 ml dioxane, cooled to 20° C. was added 1.01 g triethylamine dropwise over a period of 2 minutes. The exotherm caused the temperature to rise to 31° C. The reaction mixture was stirred for additional 30 minutes at ambient temperature and then quenched with 300 ml of water. The precipitate formed was filtered, collected and recrystallized from acetonitrile. Wt. 1.7 g - m.p. 151°–152° C.

Analysis: Calc'd for $C_7H_9NO_2S_3Cl_3$; C, 23.6; H, 2.5; N, 7.9. Found: C, 23.8; H, 2.5; N, 8.0.

EXAMPLE II

PREPARATION OF 4-[(N-METHYL-N-TRICHLOROMETHANESULFENYL)-CARBAMOYLOXIMINO]-1,3-DITHIOLANE

To a solution of 2.3 g, 4-oximino-1,3-dithiolane and 3.86 g of N-methyl-N-trichloromethanesulfenyl-carbamylfluoride in 75 ml of dioxane, was added dropwise 1.97 g triethylamine. The ensuing exothermic reaction raised the temperature to 30° C. After stirring at ambient temperature for 30 minutes. The mixture was quenched in water. The precipitate formed was collected by filtration. The solid was dissolved in ethyl acetate, dried with magnesium sulfate and concentrated under reduced pressure. The residual solid was recrystallized from isopropylethermethylene chloride. Wt. 3.8 g - m.p. 102°–103° C.

Analysis: Calc'd for $C_6H_7N_2O_2S_3Cl_3$: C, 21.09; H, 2.06; N, 8.20. Found: C, 21.10; H, 2.14; N, 8.06.

EXAMPLE III

PREPARATION OF 2-O-[(N-METHYL-N-TRICHLOROMETHANESULFENYL) CARBAMOYLOXIMINO]-1,4-DITHIANE-4-OXIDE

To a solution of 5.0 g., 2-O-[(N-methyl-N-trichloromethanesulfenyl)-carbamoyloximino]-1,4-dithiane in 300 ml ethylacetate - methylene chloride (1:1) was added 4.69 g. of 22.8 percent peracetic acid in ethylacetate. After stirring at ambient temperature for 2 hours the reaction mixture was concentrated under reduced pressure to a residual oil. Crystallized from methanol-ethyl acetate. Wt. 4.0 g., m.p. 144°–145°.

Analysis Calc'd for $C_7H_9N_2O_2S_3Cl_3$: C, 22.62, H, 2.44, N, 7.54. Found: C, 23.11, H, 2.42, N, 7.64.

EXAMPLE IV

PREPARATION OF 2-O-[(N-METHYL-N-TRIFLUOROMETHANESULFENYL)-CARBAMOYLOXIMINO]-1,4-DITHIANE

To a solution of 2.0 g., 2-oximino-1,4-dithiane in 100 ml dioxane was added 4.85 g., 50 percent solution of N-methyl-N-trifluoromethanecarbamyl fluoride in toluene and then 1.61 g triethylamine was added dropwise with cooling and stirring. After stirring for 2 hours, it was quenched with 300 ml water. The reaction product was isolated in ethylacetate, dried over magnesium sulfate and concentrated. Crystallized from isopropylether-acetone. Wt. 3.5 g., m.p. 120°–12°.

Bean Aphid Foliage Spray Test

Adults and nymphal stages of the bean aphid (*Aphis fabae* Scop.) reared on potted dwarf nasturtium plants at 65°–70° F. and 50–70 percent relative humidity, constituted the test insects. For testing purposes, the number of aphids per pot was standardized to 100–150 by trimming plants containing excess aphids.

The test compounds were formulated by diluting the stock suspension with water to give a suspension containing 500 parts of test compound per million parts of final formulation.

The potted plants (one pot per compound tested) infested with 100–150 aphids, were placed on a revolving turntable and sprayed with 100–110 milliliters of test compound formulation by use of a DeVilbiss spray gun set at 40 psig. air pressure. This application, which lasted 25 seconds, was sufficient to wet the plants to run-off. As a control, 100–110 milliliters of a water-acetone-emulsifier solution containing no test compound were also sprayed on infested plants. After spraying, the pots were placed on their sides on a sheet of white standard mimeograph paper which had been previously ruled to facilitate counting. Temperature and humidity in the test room during the 24 hour holding period were 65°–70° F. and 50–70 percent, respectively. Aphids which fell onto the paper and were unable to remain standing after being uprighted were considered dead. Aphids remaining on the plants were observed closely for movement and those which were unable to move the length of the body upon stimulation by prodding were considered dead. Percent mortality was recorded for various concentration levels.

Southern Armyworm Leaf Spray Test

Larvae of the southern armyworm (*Prodenia eridania*, (Cram.)), reared on Tendergreen bean plants at a temperature of 80°±5° F. and a relative humidity of 50±5 percent, constituted the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100–110 milliliters of test compound formulation by use of a DeVilbiss spray gun set at 10 psig air pressure. This application, which lasted 25 seconds, was sufficient to wet plants to run-off. As a control, 100–110 milliliters of a water-acetone-emulsifier solution containing no test compound were also sprayed on infested plants. When dry, the paired leaves were separated and each one was placed in a 9 centimeter Petri dish lined with moistened filter paper. Five randomly selected larvae were introduced into each dish and the dishes were closed. The closed dishes were labeled and held at 80°–85° F. for 3 days. Although the larvae could easily consume the whole leaf within 24 hours, no more food was added. Larvae which were unable to move the length of the body, even upon stimulation by prodding, were considered dead. Percent mortality was recorded for various concentration levels.

Mexican Bean Beetle Leaf Spray Test

Fourth instar larvae of the Mexican bean beetle (*Epilachna varivestis*, Muls.), reared on Tendergreen bean plants at a temperature of 80°±5° F. and 50±5 percent relative humidity, were the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100–110 milliliters of test compound formulation by use of a DeVilbiss spray gun set at 10 psig air pressure. This application, which lasted 25 seconds, was sufficient to wet plants to run-off. As a control, 100–110 milliliters of a water-acetone-emulsifier solution containing no test compound were also sprayed on infested plants. When dry, the paired leaves were separated and each was placed in a 9 centimeter Petri dish lined with moistened filter paper. Five randomly selected larvae were introduced into each dish, and the dishes were closed. The closed dishes were labeled and held at a temperature of 80°±5° F. for 3 days. Although the larvae could easily consume the leaf within 24 to 48 hours, no more food was added. Larvae which were unable to move the length of the body, even upon stimulation, were considered dead.

Fly Bait Test

Four to 6 day old adult house flies (*Musca domestica*, L.), reared according to the specifications of the Chemical Specialities Manufacturing Association (Blue Book, McNair-Dorland Co., N.Y. 1954; pages 243–244, 261) under controlled conditions of 80°±5° F. and 50±5 percent relative humidity, were the test insects. The flies were immobilized by anesthetizing with carbon dioxide and twenty five immobilized individuals, males and females, were transferred to a cage consisting of a standard food strainer about 5 inches in diameter which was inverted over a wrapping-paper-covered surface. The test compounds were formulated by diluting the stock suspension with a 10 percent (by weight) sugar solution to give a suspension containing 500 parts of test compound per million parts of final formulation, by weight. Ten milliliters of the test formulation were added to a soufflé cup containing a 1-inch square of an absorbent cotton pad. This bait cup was introduced and centered on the blotting paper under the food strainer prior to admitting the anesthetized flies. The caged flies were allowed to feed on the bait for 24 hours, at a temperature of 80°±5° F. and the relative humidity of 50±5 percent. Flies which showed no sign of movement on prodding were considered dead.

Mite Foliage Spray Test

Adults and nymphal stages of the two-spotted mite (*Tetranychus urticae* Koch), reared on Tendergreen bean plants at 80±5 percent relative humidity, were the test organisms. Infested leaves from a stock culture were placed on the primary leaves of two bean plants 6 to 8 inches in height, growing in a 2½ inch clay pot. 150–200 Mites, a sufficient number for testing, transferred from the excised leaves to the fresh plants in a period of 24 hours. Following the 24 hour transfer period, the excised leaves were removed from the infested plants. The test compounds were formulated by diluting the stock suspension with water to give a suspension containing 500 parts of test compound per million parts of final formulation. The potted plants (one pot per compound) were placed on a revolving turntable and sprayed with 100–110 milliliters of test compound formulation by use of a DeVilbiss spray gun set at 40 psig. air pressure. This application, which lasted 25 seconds, was sufficient to wet the plants to run-off. As a control, 100–110 milliliters of a water solution containing acetone and emulsifier in the same concentrations as the test compound formulation, but containing no test compound, were also sprayed on infested plants. The sprayed plants were held at 80±5 percent relative humidity for 6 days, after which a mortality count of motile forms was made. Microscopic examination for motile forms was made on the leaves of the test plants. Any individual which was capable of locomotion upon prodding was considered living.

The results of these tests are set forth in Table I below. In these tests the pesticidal activity of the compounds against aphid, mite, Southern Armyworm, Bean Beetle and House fly was rated as follows:

A = excellent control
B = partial control
C = no control
Dashes indicate no test conducted.

Certain of these compositions were also evaluated to determine their peroral toxicity to mammals. The animal selected for this experiment was the rat. The test results obtained are expressed in terms of the number of milligrams of composition per kilogram of weight of the animal required to achieve a mortality rate of 50 percent ($LD_{50}$).

The results of these tests are set forth in Table I below:

TABLE I

| Compound | | m.p. °C | Aphid | Mite | Armyworm | Bean beetle | Housefly | Rat P.O. $LD_{50}$ mg/kg |
|---|---|---|---|---|---|---|---|---|
| I | 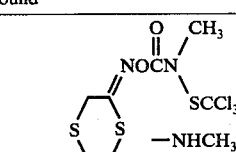 | 151–152° | | | | | | |
| | (SCCl₃) | | A | A | A | A | A | 149. |
| | (–NHCH₃) | | A | A | A | A | A | 15 |
| II | 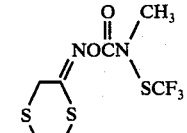 | 120–121° | A | A | A | A | A | |

TABLE I-continued

| Compound | m.p. °C | Aphid | Mite | Army-worm | Bean beetle | House-fly | Rat P.O. LD$_{50}$ mg/kg |
|---|---|---|---|---|---|---|---|
| III (—SCCl$_3$) | 102-103° | A | A | A | A | A | 75. |
| III (—NHCH$_3$) |  | A | A | A | A | A | 13. |
| IV (—SCCl$_3$) | 120-121.5° | A | A | C | A | A | — |
| IV (—NHCH$_3$) |  | A | A | B | A | A | — |
| V (—SCCl$_3$) | 132-134° | A | A | A | A | B | 7.07 |
| V (—NHCH$_3$) |  | A | A | A | A | A | 0.3 |
| VI (—SCCl$_3$) | 132-135° | A | A | A | A | A | — |
| VI (—NHCH$_3$) |  | A | A | A | A | A | — |
| VII (—SCCl$_3$) | 80-82° | B | C | C | A | A | — |
| VII (—NHCH$_3$) |  | A | C | C | A | A | — |
| VIII (—SCCl$_3$) | 144-145° | A | A | A | A | A | 28.3 |
| VIII (CH$_3$NH—) |  | C | A | A | A | A | 12.3 |
| IX (—SCCl$_3$) | 120-121° | A | A | A | A | A | — |
| IX (CH$_3$NH—) |  | A | A | A | A | A | — |

In the above Table, A indicates excellent control, B indicates partial control and C indicates no control. For comparison purposes, there is provided immediately below the data presented for the trihalomethanesulfenyl derivative the activity measurements achieved from the corresponding methyl-carbamoyl derivative adjacent to the chemical designation —NHCH$_3$. It will be observed from the pesticidal data given that the activity of the trihalomethanesulfenyl compounds is essentially equivalent to that of the corresponding methyl carbamoyl derivatives. However, the mammalian toxicity of the trihalomethanesulfenyl compositions is dramatically reduced in comparison to the toxicity of the methylcarbamoyl compositions.

To more clearly illustrate the advantages in the trichloromethanesulfenyl derivatives over their corresponding methylcarbamoyl composition, there is set forth in Table II below, a comparison of insect toxicity values obtained following the procedures described above, expressed in terms of parts per million of composition required to achieve a insect mortality of 50 percent (LD$_{50}$).

TABLE II

| Compound | Insect Toxicity, $LD_{50}$, ppm | | | | | Rat P.O. $LD_{50}$ |
|---|---|---|---|---|---|---|
| | Aphid | Mite | Army-worm | Mexican Bean beetle | House fly | |
| A. ![structure A with NOCNHCH3, dithiolane] | 5 | 6 (12)* | 53 | 52 | 1 | 15 |
| B. ![structure B with NOCN(CH3)SCCl3, dithiolane] | 13 | 7 (3)* | 52 | 10 | 2 | 149 |

*( ) systemic activity

It is considered significant to observe that the insert toxicity of the trichloromethanesulfenyl derivative is essentially equivalent to that of the methylcarbamoyl composition in all cases except the bean-beetle where a five-fold improvement was observed. It is extremely important to note that the mammalian toxicity of the trichloromethane sulfenyl composition is only 1/10th that of the methylcarbamoyl compound. The trichloromethanesulfenyl composition also had a higher degree of systemic activity.

The $LD_{50}$ values shown in the above Table II were determined by testing the compositions over an appropriate concentration range obtained by serial dilution of the stock suspension with water. The percent kill was plotted on log-probit graph paper versus parts per million concentration, and the $LD_{50}$ read from an eye-fitted line drawn through the resultant points.

Systemic treatments were made by drenching 20 milliliters of the test compound formulation into the soil around the roots of bean plants growing in 2½ inch clay pots. These pots were held in 4 ounce wax paper containers to prevent cross-contamination and loss by leaching. The plants were 4 inches high at the time of treatment and had been infested with mites 24 hours previously. Subsequent steps for testing of the systemic miticidal activity were the same as those described above for the spray method of application.

What is claimed is:

1. A compound of the formula:

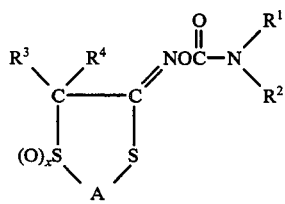

wherein:
$R^1$ is lower alkyl having from 1 to 4 carbon atoms, phenyl, or phenyl substituted with one or more halogen, acylamido, methylthio, methoxy, or alkyl substituents having from 1 to 4 carbon atoms or a methylenedioxy group attached to adjacent carbon atoms of said phenyl;

$R^2$ is trihalomethanesulfenyl;

$R^3$ and $R^4$ may be the same or different and are hydrogen, lower alkyl having from 1 to 6 carbon atoms, lower alkenyl having from 2 to 6 carbon atoms, halogen substituted alkyl having from 1 to 6 carbon atoms, alkoxyalkyl having a total of from 2 to 6 carbon atoms, alkylthioalkyl, alkylsulfinylalkyl, or alkylsulfonylalkyl, having a total of from 2 to 6 carbon atoms, phenyl or phenyl substituted with one or more halogen, methoxy or lower alkyl substituents having from 1 to 4 carbon atoms;

A is methylene, ethylene, propylene, ethenylene, propenylene or methylene, ethylene, propylene, ethenylene or propenylene substituted with one or more alkyl groups having from 1 to 3 carbon atoms; and $x$ is 0, 1 or 2.

2. A compound as claimed in claim 1 wherein A is methylene.

3. A compound as claimed in claim 1 wherein A is ethylene.

4. A compound as claimed in claim 1 wherein $R^2$ is trifluoromethanesulfenyl and $R^1$ is methyl.

5. A compound as claimed in claim 1 wherein $R^2$ is trichloromethanesulfenyl and $R^1$ is methyl.

6. A compound as claimed in claim 1 wherein $x$ is 0.

7. A compound as claimed in claim 1 wherein $x$ is 1.

8. A compound as claimed in claim 1 wherein $x$ is 2.

9. A compound as claimed in claim 1 wherein $R^3$ and $R^4$ are individually hydrogen or alkyl.

10. 5,5-Dimethyl-4-[(N-methyl-N-trichloromethanesulfenyl)-carbamoyloximino]-1,3-dithiolane.

11. 2-[(N-methyl-N-trichloromethanesulfenyl)-carbamoyloximino]-1,4-dithiane.

12. 3-Methyl-2-[(N-methyl-N-trichloromethanesulfenyl)-carbamoyloximino]-1,4-dithiane.

13. 3,3-Dimethyl-2-[(N-methyl-N-trichloromethanesulfenyl) carbamoyloximino]-1,4-dithiane.

14. 4-[(N-methyl-N-trichloromethanesulfenyl)-carbamoyloximino]-1,3-dithiolane.

* * * * *